United States Patent [19]

Brune et al.

[11] Patent Number: 4,732,986

[45] Date of Patent: Mar. 22, 1988

[54] BENZOTHIAZOLE DERIVATIVES, PROCESSES FOR THEIR PREPARATION AND PHARMACEUTICAL COMPOSITIONS CONTAINING THESE COMPOUNDS

[75] Inventors: Kay Brune, Marloffstein; Heidrun Engler, Cadolzburg; Istvan Szelenyi, Schwaig; Peter Mörsdorf, Cadolzburg; Helmut Schickaneder, Eckental; Kurt H. Ahrens, Nuremberg, all of Fed. Rep. of Germany

[73] Assignee: Ludwig Heumann & Co. GmbH, Nuremberg, Fed. Rep. of Germany

[21] Appl. No.: 51,214

[22] Filed: May 12, 1987

Related U.S. Application Data

[63] Continuation of Ser. No. 716,716, Mar. 27, 1985, abandoned.

[30] Foreign Application Priority Data

Apr. 12, 1984 [DE] Fed. Rep. of Germany ....... 3413875

[51] Int. Cl.$^4$ ............................................. C07D 277/82
[52] U.S. Cl. ..................................................... 548/161
[58] Field of Search ........................................ 548/161

[56] References Cited

U.S. PATENT DOCUMENTS

3,745,010  7/1973  Janssens ................................. 548/161
3,912,748 10/1975  Evans et al. ........................... 548/224
4,064,261 12/1977  Paget ..................................... 548/161

FOREIGN PATENT DOCUMENTS

28406  5/1981  European Pat. Off. ............. 548/161
51-35428  3/1976  Japan .................................... 548/161

*Primary Examiner*—Robert Gerstl

[57] ABSTRACT

Benzothiazole derivatives corresponding to the general formula I

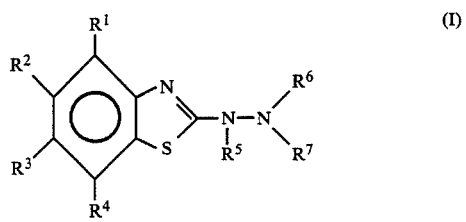

wherein $R^1$, $R^2$, $R^3$ and $R^4$ represent, independently of one another, a hydrogen atom, a halogen atom, a linear $C_1$-$C_3$-alkyl group or a linear $C_1$-$C_3$-alkoxy group, $R^5$ represents a hydrogen atom or a linear $C_1$-$C_3$-alkyl group, $R^6$ represents a hydrogen atom, and $R^7$ represents a formyl group, a carbalkoxy group of the formula

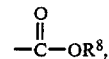

wherein $R^8$ denotes a linear or branch chained $C_1$-$C_4$-alkyl group, or it represents an acyl group of the formula

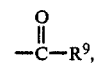

wherein $R^9$ denotes a linear $C_1$-$C_3$-alkyl group, or $R^6$ and $R^7$ together represent the group

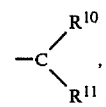

wherein $R^{10}$ and $R^{11}$ represent, independently of one another, a hydrogen atom or a linear $C_1$-$C_6$-alkyl group or $R^6$ and $R^7$ represent the group

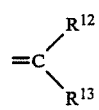

wherein $R^{12}$ and $R^{13}$ represent, independently of one another, a linear $C_1$-$C_3$-alkyl group or a linear $C_1$-$C_3$-alkoxy group or $R^6$ and $R^7$ represent the group

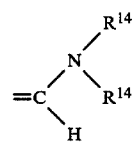

wherein $R^{14}$ denotes a linear $C_1$-$C_3$-alkyl group, as well as the physiologically acceptable salts thereof, a process for the preparation of these compounds, and a pharmaceutical preparation containing them, are described.

6 Claims, No Drawings

BENZOTHIAZOLE DERIVATIVES, PROCESSES FOR THEIR PREPARATION AND PHARMACEUTICAL COMPOSITIONS CONTAINING THESE COMPOUNDS

This application is a continuation of application Ser. No. 716,716, filed Mar. 27, 1985, now abandoned.

This invention relates to new benzothiazole derivatives, a process for their preparation, their use as pharmaceutical preparations, in particular their use as lipoxygenase inhibitors and cyclooxygenase inhibitors, pharmaceutical preparations containing these compounds, and their preparation.

It is now known that arachidonic acid metabolites such as cyclic endoperoxides, slow reacting substances of anaphylaxis (SRS-A, leucotrienes), prostaglandins and thromboxans take part in the genesis of inflammatory and allergic processes. These metabolites are formed by the enzymes lipooxygenase and cycloxygenase. It is therefore advantageous to develop medicaments containing active ingredients which have a more comprehensive antiphlogistic action than those known hitherto. Relatively few compounds having a selective action on lipoxygenase or capable of inhibiting both lipoxygenase and cyclooxygenase are known to this day. Known inhibitors of this type are, for example, benoxaprofene and 3-amino-1-(3-trifluoromethylphenyl)-pyrazoline.

It is surprisingly found that the benzothiazole derivatives which may be used according to the invention have a powerful inhibitory action which in some cases is a highly selective action on the enzyme lipoxygenase at concentrations at which cyclooxygenase is unaffected while some benzothiazole derivatives inhibit both enzymes, lipoxygenase and cyclooxygenase. The cyclooxygenase and/or lipoxygenase inhibiting benzothiazole derivatives according to the invention may therefore be used as medicaments for the treatment of inflammatory and allergic conditions.

It is an object of the present invention to provide new inhibitory substances with improved activity for the enzymes cyclooxygenase and/or lipoxygenase.

This problem is solved by the present invention.

The invention relates to benzothiazole derivatives corresponding to the general formula I

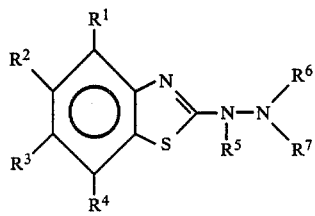

(I)

wherein $R^1$, $R^2$, $R^3$ and $R^4$ represent, independently of one another, a hydrogen atom, a halogen atom, a linear $C_1$-$C_3$-alkyl group or a linear $C_1$-$C_3$-alkoxy group, $R^5$ represents a hydrogen atom or a linear $C_1$-$C_3$-alkyl group, $R^6$ represents a hydrogen atom and $R^7$ represents a formyl group, a carbalkoxy group of the formula

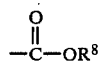

wherein $R^8$ denotes a linear or branch chained $C_1$-$C_4$-alkyl group, or an acyl group of the formula

wherein $R^9$ denotes a linear $C_1$-$C_3$-alkyl group, or $R^6$ and $R^7$ together represent the group

wherein $R^{10}$ and $R^{11}$ denote, independently of one another, a hydrogen atom or a linear $C_1$-$C_6$-alkyl group, or $R^6$ and $R^7$ represent the group

wherein $R^{12}$ and $R^{13}$ denote, independently of one another, a linear $C_1$-$C_3$-alkyl group or a linear $C_1$-$C_3$-alkoxy group, or $R^6$ and $R^7$ represent the group

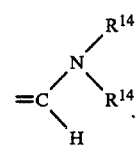

wherein $R^{14}$ denotes a linear $C_1$-$C_3$-alkyl group, and the physiologically acceptable salts thereof.

In the general formula I, $R^1$, $R^2$, $R^3$ and $R^4$ represent, independently of one another, a hydrogen atom, a halogen atom, e.g. a fluorine, chlorine or bromine atom, chlorine being preferred, a linear $C_1$-$C_3$-alkyl group, for example a propyl, ethyl or methyl group, or a linear $C_1$-$C_3$-alkoxy group such as a propoxy, ethoxy or methoxy group. $R^5$ denotes a hydrogen atom or a linear $C_1$-$C_3$-alkyl group as defined above. $R^6$ denotes a hydrogen atom. $R^7$ denotes a formyl group, a carbalkoxy group of the formula

wherein $R^8$ denotes a linear or branch chained $C_1$-$C_4$-alkyl group, e.g. a butyl, propyl, ethyl or methyl group, or an acyl group of the formula

wherein $R^9$ denotes a linear $C_1$-$C_3$-alkyl group, such as a propyl, ethyl or methyl group. Furthermore, $R^6$ and $R^7$ may together represent the group

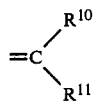

wherein $R^{10}$ and $R^{11}$ denote, independently of one another, a hydrogen atom or a linear $C_1$–$C_6$-alkyl group, preferably a linear $C_1$–$C_4$-alkyl group, in particular a linear $C_1$–$C_3$-alkyl group. Examples of these groups conform to the definition given above. Furthermore, $R^6$ and $R^7$ may together represent the group

wherein $R^{12}$ and $R^{13}$ denote, independently of one another, a linear $C_1$–$C_3$-alkyl group or a linear $C_1$–$C_3$-alkoxy group. Examples of these groups conform to the above definition.

Lastly, $R^6$ and $R^7$ may together represent the group

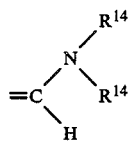

wherein $R^{14}$ denotes a linear $C_1$–$C_4$-alkyl group as defined above.

A preferred group of the compounds according to the invention is characterised in that $R^1$ to $R^4$ each represent a hydrogen atom, $R^5$ represents a linear $C_1$–$C_3$-alkyl group, in particular a methyl or ethyl group, and $R^6$ and $R^7$ together represent the group

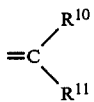

wherein $R^{10}$ preferably denotes a hydrogen atom or a linear $C_1$–$C_6$-alkyl group, preferably a methyl group, and $R^{11}$ denotes a linear $C_1$–$C_6$-alkyl group, in particular a methyl group.

Another preferred group of compounds according to the invention is characterised in that $R^1$ to $R^4$ are hydrogen atoms, $R^5$ is a hydrogen atom or in particular, a linear $C^1$–$C_3$-alkyl group, the methyl and ethyl group being particularly preferred, and $R^6$ and $R^7$ together represent the group

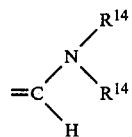

wherein $R^{14}$ denotes a linear $C_1$–$C_3$-alkyl group, in particular a methyl or ethyl group.

Furthermore, when $R^1$ to $R^4$ in the general formula I each represent a hydrogen atom, then $R^5$ is preferably a linear $C_1$–$C_3$-alkyl group, in particular a methyl group, $R^6$ a hydrogen atom and $R^7$ a formyl group, a carbalkoxy group of the formula

or an acyl group of the formula

wherein $R^8$ and $R^9$ have the meanings indicated above, preferably a formyl group.

Other preferred compounds according to the invention are characterised in that $R^1$ to $R^4$ each represent, independently of one another, a hydrogen atom, a halogen atom, a linear $C_1$–$C_3$-alkyl group or a linear $C_1$–$C_3$-alkoxy group.

Another preferred group of compounds according to the invention is characterised in that $R^1$ and $R^4$ each represent a hydrogen atom and $R^2$ and $R^3$ represent, independently of one another, a halogen atom, in particular a chlorine atom, a linear $C_1$–$C_3$-alkyl group, preferably a methyl or ethyl group, or a linear $C_1$–$C_3$-alkoxy group, in particular a methoxy or ethoxy group.

In another preferred group of compounds, $R^1$ or $R^4$ represents a halogen atom, in particular a chlorine atom, a linear $C_1$–$C_3$-alkyl group, preferably a methyl group, or a linear $C_1$–$C_3$-alkoxy group, in particular a methoxy or ethoxy group, while $R^2$ and $R^3$ preferably each denote a hydrogen atom.

$R^5$, $R^6$ and $R^7$ have the meanings indicated in claim 1 although $R^5$ in particular denotes a hydrogen atom or a $C_1$–$C_3$-alkyl group, preferably a methyl group, and $R^6$ and $R^7$ preferably represent the group

wherein $R^{10}$ denotes a hydrogen atom or a $C_1$–$C_3$-alkyl group, preferably a methyl group, and $R^{11}$ denotes a $C_1$–$C_3$-alkyl group, in particular a methyl group.

Other preferred groups of compounds according to the invention are characterised in that $R^1$ and $R^4$ are each a hydrogen atom, and $R^2$ and $R^3$ represent, independently of one another, a halogen atom, in particular a chlorine atom, a linear $C_1$–$C_3$-alkyl group, preferably a methyl or ethyl group, or a linear $C_1$–$C_3$-alkoxy group, in particular a methoxy or ethoxy group. In these cases, $R^5$ represents a hydrogen atom or, in particular, a $C_1$–$C_3$-alkyl group, preferably a methyl group, and $R^6$ and $R^7$ together represent the group

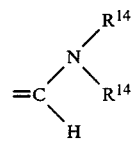

wherein $R^{14}$ is a $C_1$–$C_3$-alkyl group, preferably a methyl group.

The compounds according to the invention are prepared by a process which is characterised in that (a) a benzothiazole derivative corresponding to the general formula II

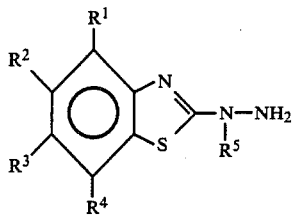 (II)

wherein $R^1$ to $R^5$ have the meanings indicated in claim 1 is reacted with aqueous formic acid, preferably in a molar ratio of 1:4 for ½ to 1 hour at 80°–100° C., preferably at 100° C., to form the compounds according to the invention corresponding to the general formula I in which $R^6$ denotes a hydrogen atom and $R^7$ a formyl group;

(b) a benzothiazole derivative corresponding to the general formula III

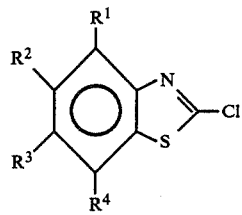 (III)

wherein $R^1$ to $R^4$ have the meanings indicated in claim 1, is reacted with a compound corresponding to the general formula IV

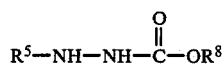 (IV)

wherein $R^5$ has the meaning indicated in claim 1 and $R^8$ represents a linear or branched chained $C_1$–$C_4$-alkyl group, the reaction being carried out for 8 to 14 hours, preferably 12 hours, as an alkaline catalysed reaction in an alcoholic solvent such as, for example, a methanol or ethanol, at the reflux temperature of the solvent used, to produce the compounds according to the invention corresponding to the general formula I wherein $R^6$ denotes a hydrogen atom and $R^7$ denotes a carbalkoxy group of the formula

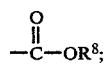

(c) a benzothiazole derivative corresponding to the general formula II

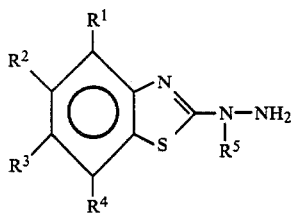 (II)

wherein $R^1$ to $R^5$ have the meanings indicated in claim 1, is reacted with a carboxylic acid corresponding to the general formula V

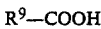 (V)

wherein $R^9$ denotes a linear $C_1$–$C_3$-alkyl group for 4 to 5 hours at 80°–100° C., preferably at 80° C., to produce the compounds according to the invention corresponding to the general formula I wherein $R^6$ denotes a hydrogen atom and $R^7$ an acyl of the formula

(d) a benzothiazole derivative corresponding to the general formula II

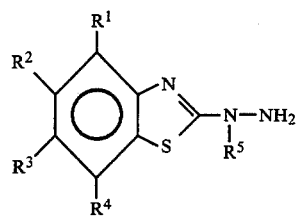 (II)

wherein $R^1$ to $R^5$ have the meanings indicated in claim 1, is reacted with a carbonyl compound corresponding to the general formula VI

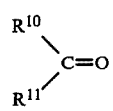 (VI)

wherein $R^{10}$ and $R^{11}$ represent, independently of one another, a hydrogen atom or a linear $C_1$–$C_6$-alkyl group for 5 to 15 hours at 20°–40° C., preferably at room temperature, to produce the compounds according to the invention corresponding to the general formula I wherein $R^6$ and $R^7$ together represent the group

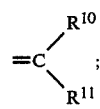

(e) a benzothiazole derivative corresponding to the general formula II

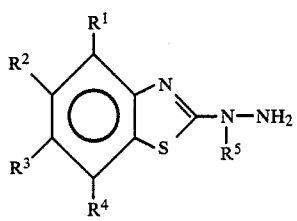 (II)

wherein $R^1$ to $R^5$ have the meanings indicated in claim 1, is reacted with an alkyl-ortho-ester derivative corresponding to the general formula VII

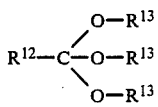 (VII)

wherein $R^{12}$ and $R^{13}$ denote, independently of one another, a linear $C_1$-$C_3$-alkyl group for 1-3 hours, preferably 2 hours, at 50°-100° C., preferably at 80° C., to produce the compounds according to the invention corresponding to the general formula I wherein $R^6$ and $R^7$ together represent the group

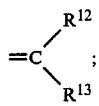

(f) a benzothiazole derivative corresponding to the general formula II

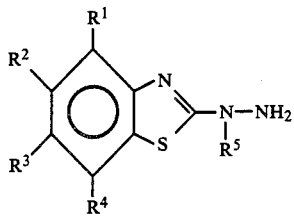 (II)

wherein $R^1$ to $R^5$ have the meanings indicated in claim 1, is reacted with a dialkylaminoacetal corresponding to the general formula VIII

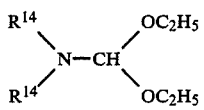 (VIII)

wherein $R^{14}$ denotes a linear $C_1$-$C_3$-alkyl group for 3-5 hours, preferably for 2 hours, at a temperature of from 80° to 120° C., preferably at 110° C., to produce a compound according to the invention corresponding to the general formula I wherein $R^6$ and $R^7$ together represent the group

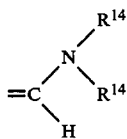

and the derivatives obtained are optionally converted into their physiologically acceptable salts.

Isolation of the compounds according to the invention and the preparation of their physiologically acceptable salts are carried out in known manner.

The compounds according to the invention may be converted into their physiologically acceptable salts with suitable acids. This reaction is carried out in known manner.

Both inorganic and organic acids are suitable. Hydrochloric acid and hydrobromic acid are examples of suitable inorganic acids. Oxalic acid, malic acid and succinic acid are examples of suitable organic acids. Any inorganic and organic acids suitable for use in pharmacology may in principle be used for the conversion of the compounds into their physiologically acceptable salts.

The compounds according to the invention corresponding to the general formula I form acid addition salts and may occur in their tautomeric forms. The present invention therefore also covers the tautomeric forms of the compounds corresponding to the general formula I.

The compounds according to the invention, preferably in the form of the salt, may be made up to any desired formulation for administration. The invention therefore also covers pharmaceutical preparations containing at least one compound according to the invention for use in human or veterinary medicine. Such pharmaceutical preparations are conventionally prepared with the aid of one or more pharmaceutically acceptable excipients or diluents.

The compound used according to the invention is preferably administered orally. The oral daily dose is normally about 0.05-100 mg per kilogram of body weight, preferably 0.1-10 mg per kilogram of body weight but it may be necessary in individual cases to deviate from these quantities, depending on the individual response to the active ingredient or the nature of its formulation and the time or interval of time at which the substance is administered. Thus, for example, there are cases where less than the minimum quantity indicated above may be sufficient whereas in other cases it will be necessary to exceed the upper limit mentioned above. When large quantities are to be administered, it may be advisable to split them up into several individual doses per day.

For oral administration, the active ingredient may be formulated, for example, in the form of capsules which are prepared by conventional methods, using pharmaceutically acceptable excipients, for example binders (such as pregelatinized corn starch, polyvinyl pyrrolidone or hydroxypropyl methyl cellulose), fillers (such as lactose, microcrystalline cellulose or calcium phosphate), lubricants (such as magnesium stearate, talcum, or silica), bursting agents (for example, potato starch or sodium starch glycollate) or moistening agents (for example, sodium lauryl sulphate).

Liquid preparations for oral administration or for direct drip feeding may take the form, for example, of solutions, syrups or suspensions or they may be presented as a dry product to be reconstituted with water or some other suitable carrier before use. Such liquid preparations may be prepared by conventional methods using pharmaceutically acceptable additives, for example, dispersing agents such as sorbitol syrup, methyl cellulose or hydrogenated edible fats, emulsifying agents, for example, lecithin or acacia, non-aqueous vehicles for example, almond oil, oily esters or ethyl alcohol, and preservatives, for example, methyl or propyl parahydroxybenzoates or sorbic acid.

For buccal administration, the preparations may be presented in the form of tablets or lozenges to be sucked. These are formulated by conventional methods.

The compounds used according to the invention may be formulated for parenteral administration by injection or for infusion. Preparations for injection may be prepared in the form of unit doses, for example in ampoules, or they may be provided in multiple dose containers with the addition of a suitable preservative.

The preparations may also assume forms such as suspensions, solutions or emulsions in oily or aqueous vehicles and they may contain formulating agents such as dispersing agents and/or stabilizers.

Alternatively, the active ingredient may be presented in powder form to be reconstituted before use with a suitable carrier such as sterile, pyrogen-free water.

The following pharmacological tests carried out on the compounds according to the invention disclose their surprising antiphlogistic activity.

1. Rat's paw oedema test
1.1 Method

An acute inflammatory oedema of the paws was induced in male rats (100–120 g) by subplantar injection of 0.1 ml of 2% carrageenin (dissolved in aqueous 0.9% NaCl solution). The volume of the paws was measured with a volumetric paw measuring apparatus 1 hour and 4 hours after the carrageenin injection. The differences between the two measurements of the paws was calculated. The test substances were suspended in 1% tylose and administered intragastrally through a stomach tube one hour after the carrageenin injection. The control animals were only given the vehicle (1% tylose). The percentage inhibition of the increase in volume in the treated animals was obtained by a comparison with the untreated controls. The average inhibitory doses ($ED_{50}$) were calculated by means of the regression curves.

1.2 $ED_{50}$ values

TABLE 1

| Example No. | $ED_{50}$ (mg/kg) |
|---|---|
| 1 | 14 |
| 2 | 15 |
| 4 | 50 |
| 5 | 25 |
| 6 | 50 |
| 7 | 25 |
| 8 | ca. 80 |

2. Leucocyte migration test
2.1 Method

A polyester sponge impregnated with 2% carrageenin solution was implanted subcutaneously in the neck region in male rats (140–150 g) (see G. A. Higgs et al, Eur. J. Pharmacol. 66, 81 (1980), A. W. Ford-Hutchinson et al, J. Pharmacol. Methods 1, 3 (1978)). The sponges were removed after 24 hours. The leucocytes which had migrated in were washed out in a PBS solution (pH 7.4, 0.5% trypsin, 10 units/ml of heparin) at 37° C. for 30 minutes.

The sponges were then carefully pressed out and centrifuged (10 minutes, 500 revs/min). The leucocytes in the washing liquid were then counted. The test substances, which were taken up in 1% tylose, and the vehicle (1% tylose) were administered intragastrally with a stomach tube immediately after implantation of the sponge and after 5 hours and 21 hours. The percentage inhibition of leucocyte migration after administration of the test substances was compared with that of the controls. The average inhibitory doses ($ED_{50}$) were calculated by means of the regression graphs.

2.1 Inhibitory action

TABLE 2

| Example No. | Dose (i.g.) | Inhibition of leucocyte migration (control = 0%) |
|---|---|---|
| 1 | 50 mg/kg | 25% |

TABLE 2-continued

| Example No. | Dose (i.g.) | Inhibition of leucocyte migration (control = 0%) |
|---|---|---|
| 4 | 50 mg/kg | 50% |
| 5 | 50 mg/kg | 30% |

3. Inhibition of PGE 2- and LTC 4-synthesis and -release
3.1 Method

The in vitro activity of the compounds according to the invention is demonstrated by known methods (see K. Brune et al, Nature 274, 262 (1978); K. Brune et al, Naunyn Schmiedeberg's Arch. Pharmacol. 315, 269 (1981); B. A. Peskar et al (1979) in: Radioimmunoassay of drugs and hormones in cardiovascular medicine, Eds. A. Albertini, M. Da Prada, B. A. Peskar, Elsevier, Amsterdam)

3.2 Inhibitory action

| | $PGE_2$ (% of controls at) | | | $LTC_4$ (% of controls at) | | |
|---|---|---|---|---|---|---|
| | $10^{-4}$ | $10^{-5}$ | $10^{-6}$ | $10^{-4}$ | $10^{-5}$ | $10^{-6}$ |
| Example 1 | 29 | 84 | 99 | 51 | >100 | >100 |

Example 1 shows a cyclooxygenase inhibitor with lipoxygenase inhibition at $10^{-4}$. The other Examples show similar pharmacological effects.

EXAMPLE 1

Preparation of $N^1$-(benzothiazol-2-yl)-$N^3$,$N^3$-dimethylformamidrazone

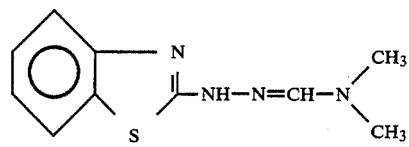

15.28 g (92.5 mmol) of 2-hydrazino-benzothiazole and 40.80 g (277.5 mmol) of N,N-dimethylformamidediethylacetal are heated to 110° C. under a nitrogen atmosphere for 2 hours. The solid which precipitates is suction filtered and recrystallised from isopropanol.

Colourless crystals, melting point 170°–172° C.
Yield: 12.55 g (62% of theoretical).
Rf=0.62 ($CH_2Cl_2$/MeOH 90:10); $C_{10}H_{12}N_4S$ (220).

| $^1H$—NMR spectrum: (d$_6$-DMSO, TMS as internal standard) | $\delta$ = 2.87(s)(—N(C$\underline{H}_3$)$_2$) 6 H, 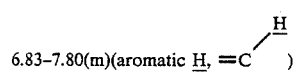 6.83–7.80(m)(aromatic $\underline{H}$, =C ) 5H, 9.70(broad)(N—$\underline{H}$)(replaceable by D$_2$O) 1H ppm. |
|---|---|

EXAMPLE 2

(a) Preparation of 2-$N^1$-methylhydrazinobenzothiazole

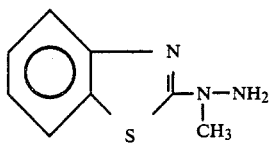

6.78 g (40 mmol) of 2-Chlorobenzothiazole are dissolved in 50 ml of ethanol and reacted with 3.7 g (80 mmol) of methylhydrazine at room temperature for 75 minutes. The crystals which precipitate when the solution is concentrated by evaporation are digested with water. The solid substance is suction filtered and dried.

Colourless crystals, melting point 134°–136° C.
Yield: 3.6 g (50.2% of theoretical).
Rf=0.3 ($CH_2Cl_2$/MeOH 95:5); $C_8H_9N_3S$ (179).

| $^1$H—NMR spectrum: ($d_6$-DMSO, TMS as internal standard) | $\delta$ = 3.37 (s)(N—C$\underline{H}_3$) 3 H, 5.43 (s)(—N$\underline{H}_2$)(replaceable by $D_2O$) 2 H, 6.87–7.80 (m)(aromatic $\underline{H}$) 4 H ppm. |
|---|---|

(b) Preparation of $N^1$-(benzothiazol-2-yl)-$N^1$,$N^3$,$N^3$-trimethylformamidrazone

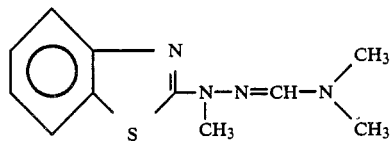

The reaction is carried out by a method analogous to that of Example 1, using 1.16 g (6.5 mmol) of 2-$N^1$-methyl-hydrazinobenzothiazole and 2.86 g (19.4 mmol) of dimethylformamide-diethylacetal.

Colourless crystals, melting point 87°–88° C.
Yield: 0.62 g (41% of theoretical).
Rf=0.58 ($CH_2Cl_2$/MeOH 90:10); $C_{11}H_{14}N_4S$ (234).

| $^1$H—NMR spectrum: (CDCl$_3$, TMS as internal standard) | $\delta$ = 2.90(s)(—N(C$\underline{H}_3$)$_2$)6H, 3.50(s)(—C$\underline{H}_3$)3H, 6.90–7.70(m)(aromatic $\underline{H}$, =C$\diagdown^{\underline{H}}$) 5H ppm. |
|---|---|

EXAMPLE 3

Preparation of $N^1$-(benzothiazol-2-yl)-$N^1$,$N^3$,$N^3$-methyldiethyl-formamidrazone

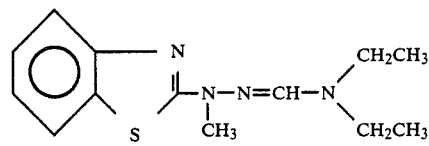

The reaction is carried out by a method analogous to that of Example 1, using 1.9 g (10.6 mmol) of 2-$N^1$-methyl-hydrazinobenzothiazole and 5.6 g (31.8 mmol) of N,N-diethyl-formamide-diethylacetal.

Light brown oil
Yield: 1.3 g (47% of theoretical).
Rf=0.24 ($CH_2Cl_2$/MeOH 98:2); $C_{13}H_{18}N_4S$ (262).

| $^1$H—NMR spectrum: (CDCl$_3$, TMS as internal standard) | $\delta$ = 1.20(t)(2 × C$\underline{H}_3$)6H, 3.30(q)(2 × C$\underline{H}_2$)4H, 3.50(s)(N—C$\underline{H}_3$)3H, 6.93–7.73(m)(aromatic-$\underline{H}$, 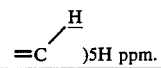)5H ppm. |
|---|---|

EXAMPLE 4

Preparation of $N^2$-(benzothiazol-2-yl)-$N^2$-methyl-formhydrazide

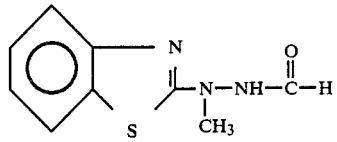

A solution of 1 g (5.6 mmol) of 2-$N^1$-methylhydrazino-benzothiazole, 1 g (21.7 mmol) of formic acid and 3.5 ml of $H_2O$ is heated to 100° C. for one hour. After cooling of the reaction solution, the colourless crystals which precipitate are suction filtered.

Colourless crystals, melting point 148°–149° C.
Yield: 0.81 g (70% of theoretical).
Rf=0.50 ($CH_2Cl_2$/MeOH 90:10); $C_9H_9N_3OS$ (207).

| $^1$H—NMR spectrum: ($d_6$-DMSO, TMS as internal standard) | $\delta$ = 3.38 (s) (—C$\underline{H}_3$) 3 H, 7.07–8.00 (m) (aromatic $\underline{H}$) 4 H, 8.30 (s) (C—$\underline{H}$) 1 H, 10.73 (s) (N—$\underline{H}$) (replaceable by $D_2O$) 1 H ppm. |
|---|---|

EXAMPLE 5

Preparation of
N²-(benzothiazol-2-yl)-ethyl-acetohydrazonate

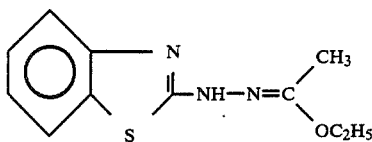

4.96 g (30 mmol) of 2-hydrazino-benzothiazole and 14.6 g (90 mmol) of ortho-acetic acid triethylester are heated to 80° C. for 2 hours. After the reaction solution has been concentrated by evaporation under vacuum, the residue is precipitated with petroleum ether and the crystals obtained are recrystallised from ethanol.

Pale pink crystals, melting point 115°–117° C.
Yield: 0.42 g (6% of theoretical).
Rf=0.42 (CH$_2$/Cl$_2$/MeOH 98:2); C$_{11}$H$_{13}$N$_3$OS (235).

| $^1$H—NMR spectrum: (d$_6$-DMSO, TMS as internal standard) | $\delta$ = 1.27 (t)(—CH$_3$) 3 H, 2.07 (s)(CH$_3$) 3 H, 4.13 (q)(—CH$_2$—) 2 H, 6.83–7.73 (m)(aromatic H) 4 H, 11.00 (s)(N—H)(replaceable by D$_2$O) 1 H ppm. |
|---|---|

EXAMPLE 6

Preparation of
N²-(6-methylbenzothiazol-2-yl)-acetohydrazide

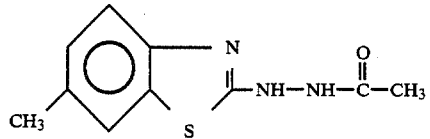

3 g (16.8 mmol) of 2-hydrazino-6-methylbenzothiazole are heated to 80° C. in 15 ml of conc. acetic acid for 5 hours. After the reaction solution has been concentrated by evaporation under vacuum, the residue is recrystallised from ethyl acetate.

Pale yellow crystals, melting point 226°–230° C.
Yield: 0.33 g (8.9% of theoretical).
Rf=0.32 (CH$_2$Cl$_2$/MeOH 90:10); C$_{10}$H$_{11}$N$_3$OS (221).
Calculated: C 54.28 H 5.01 N 18.98; Found: C 54.32 H 5.01 N 18.97.

| $^1$H—NMR spectrum: (d$_6$-DMSO, TMS as internal standard) | $\delta$ = 1.92 (s)(—CH$_3$) 3 H, 2.33 (s)(—CH$_3$) 3 H, 7.00–7.63 (m)(aromatic H) 3 H, 9.47–10.33 (2 × N—H)(replaceable by D$_2$O) 2 H ppm. |
|---|---|

EXAMPLE 7

Preparation of
N-(6-methylbenzothiazol-2-yl)acetaldehydehydrazone

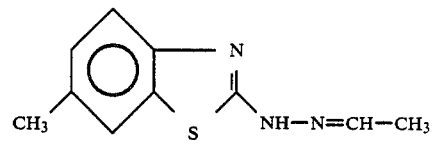

0.88 g (20 mmol) of acetaldehyde are added to 1.34 g (7.5 mmol) of 2-hydrazino-6-methylbenzothiazole in 12 ml of conc. acetic acid and the mixture is reacted at room temperature for 12 hours. After the reaction solution has been concentrated by evaporation, the residue is recrystallised several times from methanol.

Pale yellow crystals, melting point 187°–190° C.
Yield: 0.1 g (6.5% of theoretical).
Rf=0.50 (CHCl$_3$/MeOH 95:5); C$_{10}$H$_{11}$N$_3$S (205).
Calculated: C 58.51 H 5.40 N 20.47; Found: C 58.70 H 5.40 N 20.50.

| $^1$H—NMR spectrum: (CDCl$_3$, TMS as internal standard) | $\delta$ = 1.92 (d)(—CH$_3$) 3 H, 2.40 (s)(—CH$_3$) 3 H, 6.93–7.50 (m)(aromatic H,=CH) 4 H, 10.07 (s)(N—H)(replaceably by D$_2$O) 1H ppm. |
|---|---|

EXAMPLE 8

Preparation of N-(5-chlorobenzothiazol-2-yl acetaldehydehydrazone

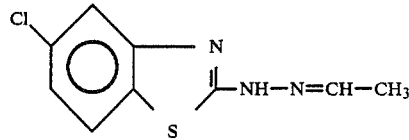

The method of preparation is analogous to that of Example 7, using 0.93 g (4.7 mmol) of 2-hydrazino-5-chlorobenzothiazole and 0.4 g (9.3 mmol) of acetaldehyde.

Pale yellow crystals, melting point 240°–242° C.
Yield: 0.50 g (47.2% of theoretical).
Rf=0.6 (CH$_2$Cl$_2$/MeOH 95:5); C$_9$H$_8$ClN$_3$S (226).

| $^1$H—NMR spectrum: (d$_6$-DMSO, TMS as internal standard) | $\delta$ = 1.95 (d) (—CH$_3$) 3 H, 6.90–7.77 (m) (aromatic H, =C$^{\diagup H}$) 4 H, 11.80 (s) (N—H) (replaceable by D$_2$O) 1 H ppm. |
|---|---|

EXAMPLE 9

Preparation of
N-(6-chlorobenzothiazol-2-yl)acetaldehydehydrazone

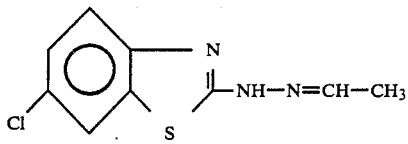

The method of preparation is analogous to that of Example 7, using 1.91 g (10 mmol) of 2-hydrazino-6-chlorobenzothiazole and 0.66 g (15 mmol) of acetaldehyde.

Pale yellow crystals, melting point 242° C.
Yield: 1.3 g (57.5% of theoretical).
Rf=0.5 ($CH_2Cl_2$/MeOH 95:5); $C_9H_8ClN_3S$ (226).

| $^1$H—NMR spectrum: ($d_6$-DMSO, TMF as internal standard) | $\delta =$ 1.93 (d) (—C$\underline{H}_3$) 3 H, 7.13–7.93 (m) (aromatic $\underline{H}$, =C$\diagup^{\underline{H}}$ ) 4 H, 11.87 (s) (N—$\underline{H}$) (replaceable by $D_2O$) 1 H ppm. |
|---|---|

EXAMPLE 10

Preparation of $N^2$-(benzothiazol-2-yl)-$N^2$-methyl acetaldehydehydrazone

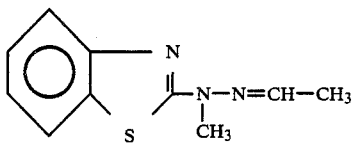

The method of preparation is analogous to that of Example 7, using 2-$N^1$-methylhydrazino-benzothiazole and acetaldehyde.

Pale yellow crystals, melting point 92°–94° C.
Rf=0.66 ($CH_2Cl_2$/MeOH 97:3); $C_{10}H_{11}N_3S$ (205).

| $^1$H—NMR spectrum: ($d_6$-DMSO, TMS as internal standard) | $\delta =$ 2.00 (d)(—C$\underline{H}_3$) 3 H, 3.53 (s)(—C$\underline{H}_3$) 3 H, 7.00–7.90 (m)(aromatic $\underline{H}$, =C$\underline{H}$) 5 H ppm. |
|---|---|

What is claimed is:

1. Benzothiazole derivatives corresponding to the general formula I

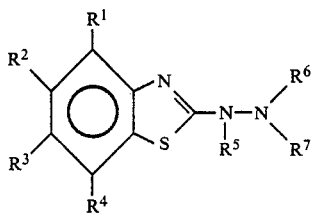

wherein
$R^1$ represents a hydrogen atom, $R^2$ represents a hydrogen or halogen atom,
$R^3$ represents a hydrogen atom, a halogen atom or a $C_1$–$C_3$ alkyl group,
$R^4$ represents a hydrogen atom,
$R^5$ represents a linear $C_1$–$C_3$ alkyl group,
$R^6$ represents a hydrogen atom, and
$R^7$ represents a formyl group; and the physiologically acceptable salts thereof.

2. Benzothiazole derivatives corresponding to the general formula I

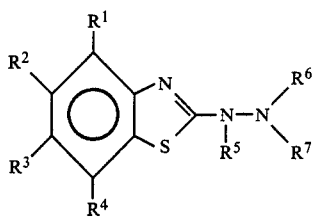

wherein
$R^1$ represents a hydrogen atom,
$R^2$ represents a hydrogen or halogen atom,
$R^3$ represents a hydrogen atom, a halogen atom or a $C_1$–$C_3$ alkyl group,
$R^4$ represents a hydrogen atom,
$R^5$ represents a hydrogen atom or a linear $C_1$–$C_3$ alkyl group, and
$R^6$ and $R^7$ together represent the group

wherein $R^{12}$ represents a linear $C_1$–$C_3$-alkyl group and $R^{13}$ represents a linear $C_1$–$C_3$-alkoxy group; and the physiologically acceptable salts thereof.

3. Benzothiazole derivatives corresponding to the general formula I

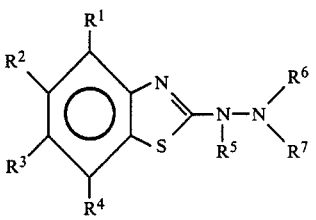

wherein
$R^1$ represents a hydrogen atom,
$R^2$ represents a hydrogen or halogen atom,
$R^3$ represents a hydrogen atom, a halogen atom or a $C_1$–$C_3$ alkyl group,
$R^4$ represents a hydrogen atom,
$R^5$ represents a hydrogen atom or a linear $C_1$–$C_3$ alkyl group,
$R^6$ and $R^7$ together represent the group

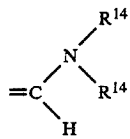

wherein $R^{14}$ denotes a linear $C_1$–$C_3$-alkyl group; and the physiologically acceptable salts thereof.

4. $N^1$-(Benzothiazol-2-yl)-$N^3$,$N^3$-dimethyl-formamidrazone and the physiologically acceptable salts thereof.

5. $N^1$-(Benzothiazol-2-yl)-$N^1$,$N^3$,$N^3$-trimethylformamidrazone and the physiologically acceptable salts thereof.

6. $N^2$-(Benzothiazol-2-yl)-$N^2$-methylformhydrazide and the physiologically acceptable salts thereof.

* * * * *